United States Statutory Invention Registration [19]

[11] Reg. Number: H571

Hollinger et al. [43] Published: Feb. 7, 1989

[54] DOUBLE-BLADED, WATER-COOLED ATTACHMENT FOR SURGICAL BONE CUTTING SAW AND METHOD FOR USING AND ASSEMBLING THE SAME

[75] Inventors: Jeffrey O. Hollinger, Glenwood; John P. Schmitz, Columbia; Eric S. Koppelman, Bowie, all of Md.

[73] Assignee: The United States of America as represented by the Secretary of the Army, Washington, D.C.

[21] Appl. No.: 831,196

[22] Filed: Feb. 20, 1986

[51] Int. Cl.[4] ..... A61B 17/14
[52] U.S. Cl. ..... 128/317; 30/123.3
[58] Field of Search ..... 128/317; 30/392, 304, 30/123.3

[56] References Cited

U.S. PATENT DOCUMENTS

| | | | |
|---|---|---|---|
| 1,530,796 | 3/1925 | Thomsen | 30/304 X |
| 1,660,015 | 2/1928 | Schimpff | 128/317 |
| 2,179,250 | 11/1939 | D'Amato | 128/317 |
| 3,126,889 | 3/1964 | Blumenfeld | 30/123.3 X |
| 3,640,280 | 2/1972 | Slanker et al. | 128/317 |
| 4,008,720 | 2/1977 | Brinckmann et al. | 128/317 |

*Primary Examiner*—Deborah L. Kyle
*Assistant Examiner*—Michael J. Carone

[57] ABSTRACT

The invention is directed to a simple attachment for a surgical bone cutting or osteotomy saw. The invention, consisting of a calibrated T-bar, saw blade holder assemblies, and cooling assemblies, permits two standard surgical saw blades to be attached in parallel to a nitrogen powered surgical reciprocating saw. Thus, a surgeon can make measured, parallel bone cuts in a single motion. The cooling assemblies, pivotally attached to the blade holder assemblies, permit water to be directed down and into the surgical site during the entire cutting operation thereby eliminating bone necrosis and reducing the risk of post-surgical bone morbidity.

9 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DOUBLE-BLADED, WATER-COOLED ATTACHMENT FOR SURGICAL BONE CUTTING SAW AND METHOD FOR USING AND ASSEMBLING THE SAME

BACKGROUND OF THE INVENTION

This invention relates to surgical instruments and, more specifically, to an attachment for a standard surgical bone cutting (osteotomy) saw.

For wounds resulting in a tearing away (avulsion) of bony structure, reconstructive surgery, bone implants, and/or grafts are needed to restore bone continuity. Furthermore, the majority of patients who undergo reconstructive facial surgery require partial or complete dentures (dental prostheses). For a dental prosthesis to fit and function properly in the mouth, there must be a successful reconstruction of a bony base ample enough to support the prosthesis. As discussed below, use of the invention will substantially increase the chances for successful reconstructive surgery in these cases.

Under current surgical procedures and technology, when a surgeon removes (ablates) a section of bone from the human body during reconstructive surgery, he or she will use a standard motor or power pack such as a nitrogen driven ZIMMER reciprocating saw. A single surgical saw blade will be attached.

Obviously, to remove a length of diseased (morbid) bone with a single bladed surgical saw will require two cuts with a measurement between them to ensure that the correct length of bone is removed. Sometimes the measurement is inaccurate and, frequently, the second cut is not parallel to the first. If a bone implant or graft is to be inserted into the host site where the diseased bone was removed, and the lengths of the site and the implant/graft do not precisely match and/or the bone walls are not exactly parallel, the complete, continuous host-graft contact which is needed for "graft-take" will be missing.

The need to make multiple cuts and measurements engendered by a single bladed surgical saw also impacts on the length of operations. Use of such a configured saw in multiple osteotomies, in particular, will substantially extend operating time.

There is an additional problem encountered when bone is cut during a surgical procedure. The heat generated by the cutting action of the saw through the bone, if above 47° C., induces bone cell death (necrosis). This can result in post-surgical bone morbidity, pain and inflammation of the bone (osteomyelitis).

Surgical instruments do exist which address, in part and piecemeal, some of the problems associated with bone surgery described above. However, no one device addresses all of these problems in a simple, lightweight, easy to use attachment as does the claimed invention. While both U.S. Pat. Nos. 1,660,015 and 2,179,250 describe devices which can make simultaneous parallel surgical bone cuts, neither has a means for cooling the bone-saw interface during the cutting operation. Furthermore, both use circular blades which together with the cumbersome nature of their design make both inappropriate for use in surgical sites around the small and delicate upper facial (maxillofacial) bones. Finally, both are powered by electric motors which cannot be used in today's operating rooms.

U.S. Pat. No. 3,640,280 shows a reciprocating surgical saw containing cooling means. However, this device cannot make parallel cuts. Furthermore, the cooling fluid is not released along the length of the saw blade and, most importantly, there is no provision for the cooling means to pivot as the surgical cuts are made thereby keeping the water directed at the surgical site throughout the cutting operation.

SUMMARY OF THE INVENTION

The problems described above are solved, to a great extent, through the practice of the invention. Illustratively, a rigid T-bar, which is calibrated, can be secured to a lightweight, nitrogen powered surgical saw. Two blade holder assemblies are then slid onto the horizontal part of the T-bar and, using the calibration markings, moved the proper distance apart and secured. Standard surgical saw blades can then be inserted into the blade holder assemblies and secured.

Finally, a cooling assembly can be pivotally attached to each blade holder assembly. Each cooling assembly consists of (1) a fluid receiver with a nipple to which a water tube can be attached and (2) an inverted U-shaped shroud with multiple openings. The shroud fits over the top and down each side of the saw blade, runs the length of the saw blade and attaches by a flexible tube to the fluid receiver.

During a cutting operation, the water flows under pressure into the fluid receiver and shroud and out the shroud openings thereby cooling the cut sites. As the blades move through the bone, the cooling assemblies pivot upwardly thereby keeping the water flowing directly down and into the surgical site.

Thus the invention provides a simple, lightweight, and relatively small attachment to a nitrogen powered reciprocating surgical saw. The simplicity of the attachmen permits rapid setup. The invention's weight and size prevents hand fatigue and permits surgery at even the most delicate of maxillofacial surgical sites.

The calibration of the T-bar and the parallel blades enable the surgeon to prepare precise, measured osteotomy cuts in one motion. Therefore, the invention substantially simplifies and speeds up osteotomy procedures and significantly shortens operating time, particularly when multiple osteotomies, such as bone implants or grafts, are required.

When implanting or grafting bone into a host site, the implant or graft can be cut with one motion and without further measurement and will precisely match the dimension of the host site. Furthermore, the bone walls at the surgical site will be parallel due to the blade arrangement thereby aiding fixation of the wall surfaces with the implant or graft ("graft-take") and speeding the healing process.

Finally, the addition of the cooling assemblies, as designed and described in detail below, will keep the bone contiguous to the saw blades both cool and moist. This will eliminate heat induced bone necrosis and substantially reduce post-surgical bone morbidity.

For a more complete appreciation of the invention, attention is invited to the following detailed description of a preferred embodiment of the invention taken with the figures of the drawings. The scope of the invention, however, is limited only through the claims appended hereto.

DETAILED DESCRIPTION OF THE PREFERRED EMBODIMENT

Figure 1:
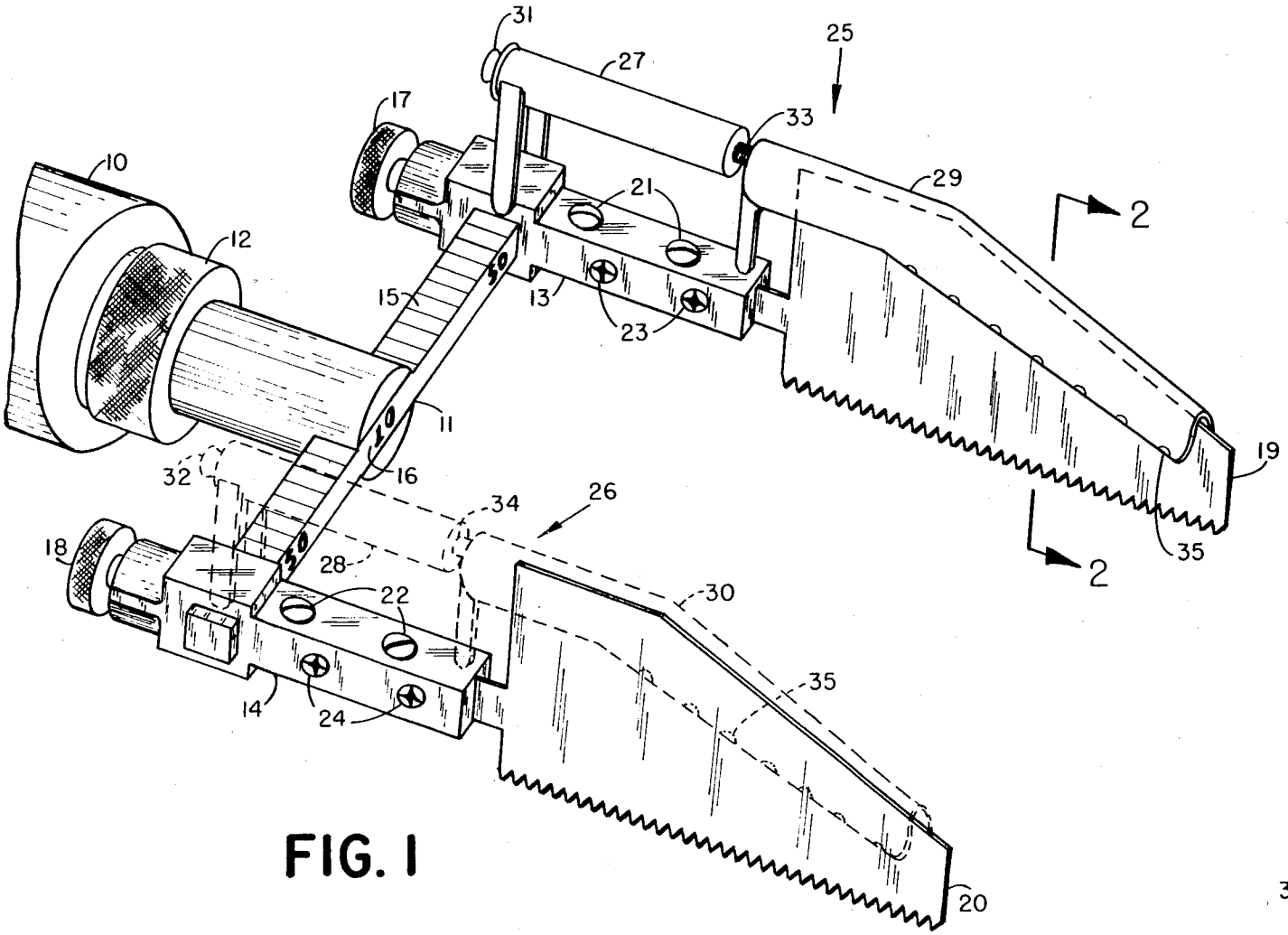
FIG. 1 illusrates a typical embodiment of the invention.

An illustrative embodiment of the invention is shown in FIG. 1 of the drawing attached to a surgical bone cutting saw motor 10, such as a standard nitrogen powered ZIMMER reciprocating saw.

In this embodiment of the invention, a rigid, one-piece T-bar 11 contains a threaded portion 12 at the bottom of the vertical part of the T-bar. This threaded portion 12 permits the T-bar 11 to be screwed on to the saw motor 10. Any number of methods could be employed to ensure that the plane in which the T-bar lies is parallel to the plane in which the saw motor trigger lies. However, in this particular embodiment, the threads in the T-bar are designed so that the final tightening of the T-bar on the surgical saw results in the T-bar and the saw motor trigger being in parallel planes. This permits rapid, accurate attachment of the T-bar 11 to the saw motor 10.

Once the T-bar 11 is attached to the saw motor 10, blade holder assemblies 13,14 are placed on the horizontal part of the T-bar, one blade holder assembly on each side of the T-bar's vertical part. This is accomplished by sliding the T-bar through a matching hole located in the rear of each blade holder assembly. The blade holder assemblies 13,14 can now be slidably moved on the T-bar 11 to the correct width required for the cutting operation.

FIG. 1 illustrates one method for calibrating the T-bar 11 to permit rapid, precise spacing of the blade holder assemblies 13,14 resulting in precise, measured, parallel cuts. Lines or indicia 15 are etched on a side of the horizontal part of the T-bar 11 a measured distance, e.g., millimeters, apart. Numbers 16 are etched in the top of the horizontal part of the T-bar 11 to permit a rapid setting of the distance between the blade holder assemblies 13,14.

Once the blade-holder assemblies 13,14 are the correct distance apart, they are secured to the T-bar with thumbscrews 17,18 which pass through the rear of the blade holder assemblies and, when tightened, press against the T-bar. The shape of the T-bar 11 and the matching holes in the blade holder assemblies 13,14 in which the T-bar slides will prevent rotation of the blade holder assemblies around the axis of the horizontal part of the T-bar.

After the blade holder assemblies 13,14 are attached to the T-bar 11, standard bone cutting or osteotomy surgical saw blades 19,20 are inserted into a slot in the front of each blade holder assembly. Two sets of screws 21,23 and 22,24 secure saw blades 19,20, respectively, in the blade holder assemblies 13,14.

As can be seen, the invention as now constructed contains parallel blades set a measured distance apart. This permits precise parallel cuts to be made in one motion and without further measurement thereby substantially reducing operating time. The accurate measurements and parallel bone walls resulting from the use of the invention are particularly helpful in ensuring the successful healing and "graft-take" in bone implant or graft cases.

The cooling assemblies 25,26 consist of hollow fluid receivers 27,28 and shrouds 29,30 which fit over the saw blades 19,20. In this embodiment of the invention the cooling assemblies are separate elements, one being attached to each blade holder assembly. However, another possible embodiment considered to be within the scope of this invention would be to construct the cooling assemblies as a single unit.

The fluid receivers 27,28 are pivotally attached to the blade holder assemblies 13,14 and are also flexibly connected to the shrouds 29,30. The fluid receivers 27,28 each have a nipple 31,32 formed at their rear for attachment of a water tube.

The connections between the fluid receivers 27,28 and the shrouds 29,30 are shown in FIG. 1. They consist of tubes 33,34 which serve the functions of holding the fluid receivers 27,28 and the shrouds 29,30 together, allowing the shrouds 29,30 to pivot about the fluid receivers 27,28, and permitting fluid to pass from the fluid receivers 27,28 to the shrouds 29,30.

In accordance with a feature of the invention, the pivot connection between the fluid receivers 27,28 and the blade holder assemblies 13,14 and the flexible connection between the fluid receivers 27,28 and the shrouds 29,30 allow the cooling assemblies 25,26 to move upward during the cutting operation and remain immediately above the cuts. This permits water to be directed into the surgical site during the entire procedure.

Figure 2:
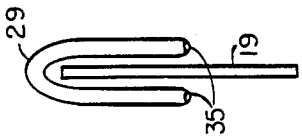
FIG. 2 illustrates a sectional view through the lines 2—2 in FIG. 1.

As shown in FIGS. 1 and 2 the shrouds are generally an inverted U-shape in design with the bottom of the U lying over the top of the saw blades 19,20 and the sides of the U extending downwardly on either side of the saw blades 19,20. In this embodiment, the shrouds 29,30 extend for almost the complete length of the saw blades 19,20. Each shroud has a plurality of openings 35 along the bottom edges on both sides of the saw blades 19,20 as can be seen in both FIGS. 1 and 2.

In operation, water tubes are attached to the nipples 31,32 on the fluid receivers 27,28. As cutting begins, the water is turned on and forced under pressure through the fluid receivers 27,28, tubes 33,34 connecting the fluid receivers 27,28 with the shrouds 29,30 and out the openings 35 in the shrouds 29,30. As the saw blades pass through bone, the cooling assemblies 25,26 will pivot up and away as they come in contact with the bone on either side of the cut.

The invention as thus described provides the surgeon with a means for making rapid, measured parallel cuts while simultaneously directing cooling water into the site of the cuts during the entire operation. As a result, operating time will be reduced and the chances for a successful bone implant or graft substantially increased. Furthermore, the heat generated by the cutting operation will be significantly reduced, bone necrosis caused by the heat will be prevented and post-surgical bone morbidity prevented or substantially reduced.

We claim:

1. An attachment for a surgical saw motor comprising:

(a) means for connecting two surgical saw blades to said saw motor, so that two parallel cuts can be made simultaneously; and (b) means for cooling said surgical saw blades and the bone areas adjacent thereto when said surgical saw blades are engaged in a cutting operation.

2. The attachment as recited in claim 1, wherein said connecting means are adjustable and calibrated, permitting variable width, measured cuts.

3. The attachment as recited in claim 1, wherein said connecting means comprises:

(a) a T-bar, attached to said saw motor, which is rigid and calibrated;

(b) two blade holder assemblies one for each of said surgical saw blades, said blade holder assemblies each containing a hole permitting said blade holder assemblies to be slidably mounted on said T-bar;

(c) means for securing said blade holder assemblies to said T-bar; and (d) means for securing said surgical saw blades to said blade holder assemblies.

4. The attachment as recited in claim 1, wherein said cooling means are pivotally attached to said connecting means, permitting said cooling means to pivot away from said surgical saw blades as said surgical saw blades are engaged in a cutting operation.

5. The attachment as recited in claim 4, wherein said cooling means are disposed along the length and both sides of each of said saw blades and contain a plurality of openings through which a fluid may be ejected.

6. The attachment as recited in claim 1, wherein said cooling means comprises:

(a) a fluid receiver hich is pivotally attached to said connecting means and contains a fluid passageway; and (b) a shroud flexibly and fluidly connected to said fluid receiver and disposed over the top and along the length and both sides of said surgical saw blades and containing a fluid passageway and a plurality of openings through which a fluid may be ejected.

7. An attachment for a reciprocating surgical saw motor comprising:

(a) a T-bar, attached to said saw motor, which is rigid and calibrated;

(b) two blade holder assemblies one for each of two surgical saw blades, said blade holder assemblies each containing a hole permitting said blade holder assemblies to be slidably mounted on said T-bar;

(c) means for securing said blade holder assemblies to said T-bar;

(d) means for securing said surgical saw blades to said blade holder assemblies;

(e) two fluid receivers each pivotally attached to one of said blade holder assemblies and each containing a fluid passageway; and (f) two shrouds each flexibly and fluidly connected to one of said fluid receivers and disposed over the top and along the length and both sides of one of said surgical saw blades and each containing a fluid passageway and a plurality of openings through which a fluid may be ejected.

8. A method of making simultaneous parallel cuts during a surgical bone cutting operation and reducing the heat in the bone generated by said cutting operation, which comprises the steps of:

(a) cutting the bone using a surgical saw motor which has two surgical saw blades connected in parallel thereto; and (b) cooling said surgical saw blades and the bone areas adjacent thereto during said cutting operation.

9. A method of assembling an attachment for a surgical saw motor, which comprises the steps of:

(a) attaching to said saw motor a T-bar which is rigid and calibrated;

(b) mounting slidably on said T-bar two blade holder assemblies one for each of two surgical saw blades;

(c) securing said blade holder assemblies to said T-bar;

(d) securing said surgical saw blades to said blade holder assemblies;

(e) attaching pivotally to each of said blade holder assemblies a fluid receiver, each of said fluid receivers containing a fluid passageway; and (f) connecting flexibly and fluidly to each of said fluid receivers a shroud, each of said shrouds being disposed over the top and along the length and both sides of one of said surgical saw blades and each of said shrouds containing a fluid passageway and a plurality of openings through which a fluid may be ejected.

* * * * *